United States Patent [19]
Wheeler

[11] 4,283,348
[45] Aug. 11, 1981

[54] METHOD OF PREPARING 2-ARYL-3-CYCLOPENTANEDIONE COMPOUNDS

[75] Inventor: Thomas N. Wheeler, Charleston, W. Va.

[73] Assignee: Union Carbide Corporation, New York, N.Y.

[21] Appl. No.: 78,923

[22] Filed: Sep. 26, 1979

Related U.S. Application Data

[62] Division of Ser. No. 944,995, Sep. 22, 1978.

[51] Int. Cl.³ .............. C07C 49/707; C07C 121/76; C07C 147/10
[52] U.S. Cl. .............................. 260/465 D; 71/123; 260/465 E; 260/465 F; 424/331; 568/29; 568/30; 568/31; 568/36; 568/37; 568/42; 568/43; 568/306; 568/314; 564/154; 564/155; 564/162; 564/163; 564/166; 564/169; 564/307
[58] Field of Search .......... 260/590 C, 465 D, 465 E, 260/465 F, 559 R, 559 A, 559 T, 570.8 R, 571; 568/29, 30, 31, 36, 37, 42, 43, 306, 314

[56] References Cited

U.S. PATENT DOCUMENTS

| 3,784,605 | 1/1974 | Durden et al. ................ 260/590 C |
| 3,801,630 | 4/1974 | Diehl et al. .................... 260/551 S |
| 3,803,240 | 4/1974 | Durden et al. ................ 260/590 C |
| 3,852,359 | 12/1974 | Dunbar et al. ................ 260/590 C |
| 3,922,307 | 11/1975 | Müller ............................... 568/314 |
| 3,954,998 | 5/1976 | Durden et al. ....................... 424/331 |
| 4,041,049 | 8/1977 | Müller et al. ................... 260/343.5 |

OTHER PUBLICATIONS

Eskola, Chemical Abstracts, vol. 32, 3359–3360 (1938).
Eskola, Chemical Abstracts, vol. 41, 949–950 (1947).
Gren et al., Chemical Abstracts, vol. 56, 2391 (1962).
Gren et al., Chemical Abstracts, vol. 58, 8990 (1963).
Betts et al., J. Chem. Soc., pp. 3333–3340 (1961).
Durden, Medical Chemistry IV, Proceedings of the 4th International Symposium on Medical Chemistry, pp. 143–171 (1974).

Primary Examiner—Dolph H. Torrence
Attorney, Agent, or Firm—Dale Lynn Carloon; Clement J. Vicari

[57] ABSTRACT

2-Aryl-1,3-cyclopentanedione compounds and their alkali metal and ammonium salts exhibit outstanding herbicidal and acaricidal activity.

2 Claims, No Drawings

METHOD OF PREPARING 2-ARYL-3-CYCLOPENTANEDIONE COMPOUNDS

This application is a division of our prior U.S. application Ser. No. 944,995 filed 9-22-78 pending.

This invention relates to 2-aryl-1,3-cyclopentanedione compounds and methods of preparing them. In another aspect this invention is directed to acaricidal, post-emergent herbicidal and pre-emergent herbicidal compositions comprising an acceptable carrier and a pesticidally effective amount of a compound of this invention or a mixture of said compounds. This invention further relates to methods of controlling acarids and plant pests which comprises subjecting the acarids and the plant pest to a pesticidally effective amount of a compound of this invention or a mixture of said compounds.

More particularly, this invention relates to compounds of the formula:

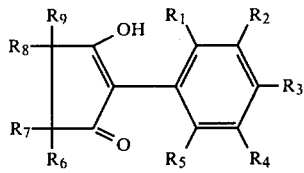

and alkali metal and ammonium salts thereof, wherein:

$R_1$ is an alkyl, halogen, haloalkyl or polyhaloalkyl group;

$R_2$, $R_3$, $R_4$, and $R_5$, are individually hydrogen, haloalkyl, polyhaloalkyl, halogen, cyano, alkoxy, alkyl, nitro, alkylsulfnyl, alkylsulfinyl, alkylthio, alkanoyl, amino or amide group;

$R_6$, $R_7$, $R_8$, and $R_9$ are individually hydrogen or either an unsubstituted or substituted alkyl, alkenyl, cycloalkyl, cycloalkenyl or phenyl group wherein the permissible substituents are one or more alkyl, alkenyl, cycloalkyl, cycloalkenyl, cyano, halogen, nitro, alkoxy, aryloxy, alkylthio, arylthio, alkylsulfinyl, arylsulfinyl, alkylsulfonyl, arylsulfonyl, acylamido or dialkylamino groups or any two $R_6$, $R_7$, $R_8$, or $R_9$ substituents taken together are an alkylene or alkenylene group having from 2 to 20 carbon atoms completing a 3, 4, 5, 6 or 7 membered carbon ring;

with the provisos that $R_1$, $R_2$, $R_3$, $R_4$, $R_5$, $R_6$ $R_7$, $R_8$ and $R_9$ substituents individually may not include more than ten aliphatic carbon atoms, and that an alkenylene chain formed by any two of $R_6$, $R_7$, $R_8$, or $R_9$ resulting in a six membered fused polycyclic ring structure may not have more than one double bond.

It is understood that the instant compounds are best represented as a tautomeric mixture of the following structures:

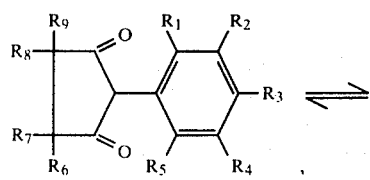 ⇌

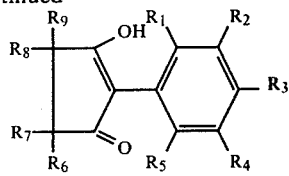

It is further understood that the ring structures formed from $R_6$, $R_7$, $R_8$ and $R_9$ taken together may be polycyclic in nature which include those of the fused and the spiro variety.

As used within this specification the prefix "aryl" designates any organic radical derived from an aromatic hydrocarbon by the removal of one hydrogen atom. Preferably, aryl designates a phenyl or a naphthyl moiety.

PREFERRED EMBODIMENT OF THE INVENTION

All compounds within the purview of the above generic formula exhibit acaridical and herbidical activity to a greater or lesser extent. Some of these compounds exhibit very high levels or acaricidal or herbicidal activity in extremely small dosages while others require larger dosages to be pesticidally effective. The compounds of the instant invention are particularly effective against mites, both in the egg stage and the adult stage. Acaricidal and herbicidal activity is greatest in those compounds having an alkyl or halogen group at one ortho position of the 2-phenyl moiety and a hydrogen, alkyl, alkoxy, cyano, trihalomethyl or halogen substituent at either the para position or the other ortho position of the 2-phenyl moiety. Especially active are those compounds in which the ortho substituents are relatively small groups such as methoxy, ethoxy, methyl, ethyl, hydrogen or halogen.

It has also been found that some of the pesticidal compositions of this invention exhibit excellent fumigant properties. Fumigant activity is defined as the ability of a pesticide to exert its pesticidal activity on an untreated surface or plant from a treated surface or plant in close proximity to the untreated area. It is believed that this property is caused, at least in part, by the low vapor pressure of the compounds allowing them to volatilize from a treated surface thereby exerting their pesticidal effects on nearby untreated areas. In addition, these compounds are relatively non-toxic to mammals when used in amounts sufficient to kill acarids or undesirable plant growth.

In addition to their utility as acaricides and herbicides, the compounds of this invention are also useful as intermediates in the preparation of other pesticidally active compounds. For example 2-(2', 4'-dimethylphenyl)-1,3-cyclopentanedione can be reacted with 2-ethylhexanoyl chloride in the presence of pyridine as solvent and acid acceptor to form 3-(2-ethylhexanoyloxy)-2-(2',4'-dimethylphenyl)-2-cyclopentenone, the corresponding pesticidally active enol ester compound. In preparing other pesticidal compounds, the compounds of this invention can also be reacted with other chemical species containing electron deficient reaction sites as, for example, organic anhydride compounds such as acetic anhydride. Certain reactions leading to the pesticidally active enol ester derivatives are described in more detail in my copending United States Patent Application Ser. No. 944,996 entitled "BIOCI- DAL 2-ARYL-1,3-CYCLOPENTANEDIONE ENOL ESTER COMPOUNDS", filed 09/22/78.

Preferred because of their higher levels of acaricidal and herbicidal activity and because of their utility as intermediates in the preparation of other pesticidally active compounds are the compounds of this invention in which:

$R_1$ is an alkyl or halogen;

$R_2$, $R_3$ and $R_5$ are individually alkyl, cyano, hydrogen, alkoxy, halogen or trihalomethyl;

$R_6$ and $R_8$ are hydrogen; and $R_7$ and $R_9$ are individually hydrogen or alkyl, particularly $C_1$-$C_4$ alkyl, most particularly methyl; or $R_7$ and $R_9$ taken together are an alkylene group containing four carbons completing a 6 membered fused polycyclic ring structure.

The most active and particularly preferred compounds are those in which:

$R_1$ is a methyl or halogen, particularly chlorine;

$R_2$, $R_4$ and $R_5$ are hydrogen;

$R_3$ is a methyl or chlorine;

$R_6$ and $R_8$ are hydrogen; and $R_7$ and $R_9$ taken together are an alkenylene group containing four carbons completing a 6 membered fused polycyclic ring structure.

The 2-aryl-1,3-cyclopentanedione compounds of this invention can be prepared by a variety of methods. Three preferred methods for preparing the compounds of this invention are illustrated by the reaction schemes set forth below in which $R_1$, $R_2$, $R_3$, $R_4$, $R_5$, $R_6$, $R_7$, $R_8$ and $R_9$ are described above except as noted and R is an organic radical preferably a $C_1$-$C_4$ alkyl group.

Method 1

Base-Promoted Cyclization of δ-Aryl Levulinic Acid Esters

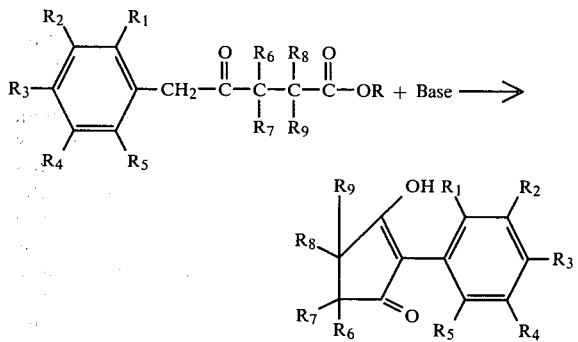

Method 1 may be utilized to make all the compounds of the instant invention.

This reaction is conducted in the presence of at least one equivalent of a strong organic or inorganic base. Illustrative of organic bases that are useful in the conduct of this reaction are the alkali metal alkoxides such as sodium methoxide, sodium ethoxide, or potassium tert-butoxide, etc. The inorganic bases would include alkali metal hydrides; such as sodium hydride, lithium hydride, etc. The preferred base is sodium ethoxide.

The reaction illustrated in Method 1 can be conducted in any solvent that is chemically inert to the reactants and to the reaction conditions. Illustrative of these solvents would be ethanol, dimethoxyethane, benzene, toluene, dimethylformamide, dimethylsulfoxide, and hexamethylphosphoric acid triamide. The preferred reaction solvent is toluene. The preferred solvent-base system is anhydrous sodium ethoxide in toluene.

The reaction of Method 1 is not pressure sensitive and may be conducted over a broad pressure range to yield the desired product. For convenience these reactions are conducted at autogeneous or atmospheric pressure. The reaction of Method 1 may be conducted over a broad range of temperatures, about 35° C. to about 200° C. Generally, these reactions are conducted at 80° C. to 120° C.

Method 2

Base-Promoted Isomerization of γ-benzylidene lactone

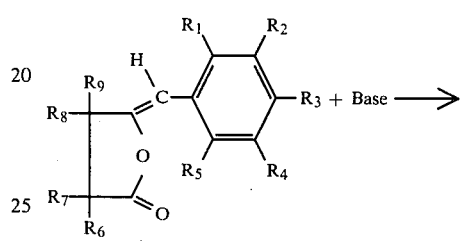

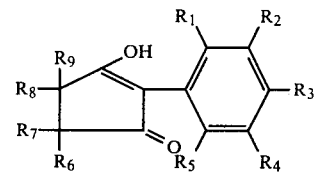

Method 2 can be used to make all the compounds of the instant invention and is especially useful in synthesizing those compounds of the instant invention where any two of $R_6$-$R_9$ substituents together form a ring.

This reaction is also conducted in the presence of at least one equivalent of a strong inorganic or organic base. Illustrative of bases that may be used are the alkali metal alkoxides, such as sodium ethoxide or potassium tert-butoxide. The preferred base is sodium ethoxide.

As with Method 1, above, the reaction of Method 2 can be conducted in any solvent that is chemically inert to the reactants and to the reaction conditions. The same solvents enumerated above for use in Method 1 may also be used in Method 2. Toluene is the preferred reaction solvent for Method 2. The preferred solvent-base combination is identical to Method 1. Again the quantity of the solvent is not critical.

The reactions of Method 2 are also not pressure sensitive and may be conducted over a broad pressure range to yield the desired product. For convenience these reactions are conducted at autogeneous or atmospheric pressure. The reactions of Method 2 may be conducted over a broad temperature range of 35° C. to about 200° C. The preferred reaction temperatures range from about 80° C. to about 120° C.

It was found with both Methods 1 and 2 that the utilization of the preferred solvent-base system, anhydrous sodium ethoxide in toluene, in the most preferred temperature range of 100° C. to 125° C. produces product yields much greater than similar reactions of the prior art.

Method 3

Pinacol Rearrangement

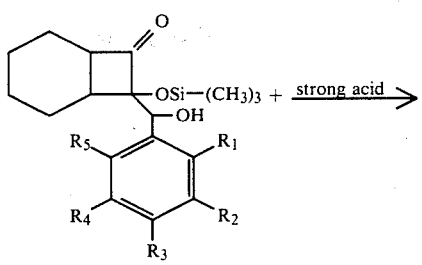

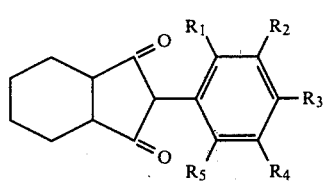

wherein preferably $R_1$, $R_2$, $R_3$, $R_4$ and $R_5$ may be a halogen, any two of $R_6$, $R_7$, $R_8$, or $R_9$ form a fused polycyclic ring structure.

Although Method 3 can be used to make all compounds of the instant invention, it is most useful, as indicated by the scheme, to synthesize those compounds where any one of the following conditions exits: (1) there is a fused ring on the cyclopentanedione moiety; (2) when the 2-phenyl substituent is itself substituted with halogens and (3) when the fused ring contains a double bond.

The pinacol rearrangement can be induced by strong acids under anhydrous conditions. The acids may be sulfuric acid, methane sulfonic acid, phosphoric acid, or trifluoroacetic acid. The preferred acid is trifluoroacetic acid without any added solvent. The reaction can be conducted between $-20°$ C. and $+70°$ C. The preferred range is $-15°$ C. to $30°$ C. Reaction is preferably performed at atmospheric pressure, although subatmospheric or superatmospheric pressure may also be used.

The alkali metal and ammonium salts of the compounds of this invention can be conveniently prepared in accordance with conventional methods. For example, the alkali metal and ammonium salts can be prepared by treating the corresponding 2-aryl-1-3-cyclopentanedione compound with an alkali metal alkoxide, or ammonia, or an amine respectively.

The δ-aryl levulinic acid esters utilized as reactants in Method 1 can be conveniently prepared via conventional esterification techniques as illustrated by the following reaction scheme:

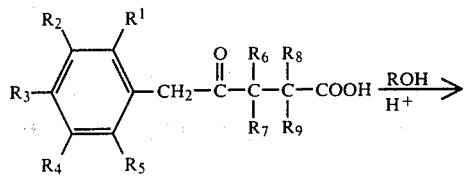

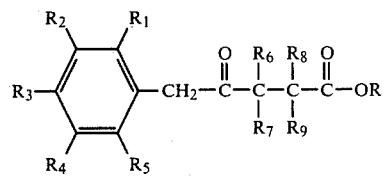

The δ-aryl levulinic acids are prepared by condensing an appropriately substituted benzyl cyanide, (A), with a suitable polyalkyl succinate ester compound, (B), in the presence of a suitable base to give the corresponding δ-cyano-δ-aryl levulinate ester (C). This ester is hydrolyzed under acid conditions to yield the desired δ-aryl levulinic acid (D). This synthesis is illustrated by the following scheme:

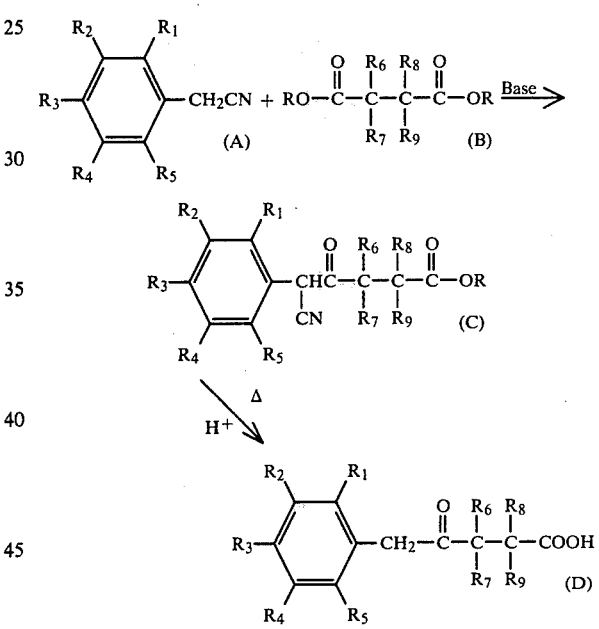

When any two of $R_6$, $R_7$, $R_8$ and $R_9$ form an alkenylene ring, the acid hydrolysis of the δ-cyano-δ-aryl levulinate ester produces the γ-benzylidene lactone used as the starting material of Method 2. The γ-benzylidene lactone can also be formed from the corresponding δ-aryl levulinic acids by an acid catalyzed lactonization:

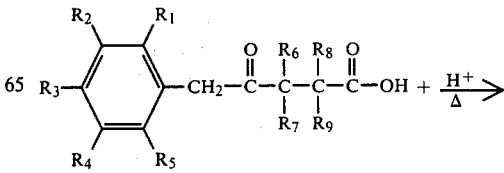

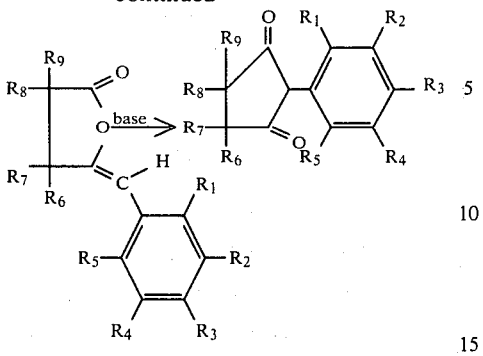

The pinacol used in Method 3 can be prepared by Lewis acid-mediated aldol condensation between bis-silylated succinoin and an aromatic aldehyde [(J. Am. Chem. Soc., 99,961 (1977)].

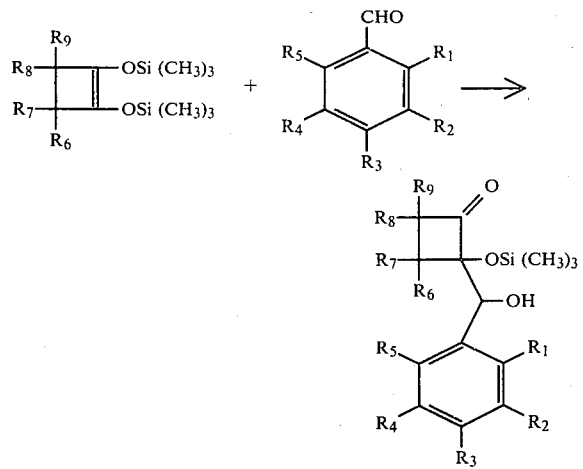

The Lewis acids used may be $TiCl_4$ or $BF_3\text{-}Et_2O$.

The bis-silylated succinoin itself can be prepared from the corresponding diethyl succinate and sodium in the presence of excess trimethylchlorosilane [*Organic Reaction*, 23, 259 (1976)]:

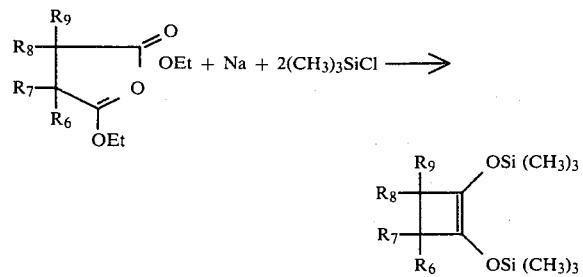

The following acaricidal and herbicidal compounds are illustrative of the compounds of the instant invention:

2-(2'-methylphenyl)-1,3-cyclopentanedione
2-(2',4'-dimethylphenyl)-1,3-cyclopentanedione
2-(2',4'dichlorophenyl)-1,3-cyclopentanedione
2-(2'-methyl-4'methoxyphenyl)-1,3-cyclopentanedione
2-(2'-chloro-5'methylsulfinylphenyl)-1,3-cyclopentanedione
2-(2'-trifluoromethylphenyl)-1,3-cyclopentanedione
2-(2'-methyl-4'-cyanophenyl)-1,3-cyclopentanedione
2-(2'-bromo-4'-benzoylphenyl)-1,3-cyclopentanedione
2-(2'chloromethyl-4'-acetamidophenyl)-1,3-cyclopentanedione
2-(2',4'-dimethyl-6'-nitrophenyl)-1,3-cyclopentanedione
2-(2'-bromo-4'-methylsulfonylphenyl)-1,3-cyclopentanedione
2-(2',4'-dimethylphenyl)-4-ethyl-1,3-cyclopentanedione
2-(2'-chloro-4'-ethylphenyl)-4-(4'-methylphenyl)-1,3-cyclopentanedione
2-(2'-methylphenyl)-4-(n-nonyl)-1,3-cyclopentanedione
2-(2'-chloro-4'-methylphenyl)-4,5-diethyl-1,3-cyclopentanedione
2-(2'-methyl-4'-methoxyphenyl)-4-cyanomethyl-1,3-cyclopentanedione
2-(2',5'-dimethylphenyl)-4-methyl-1,3-cyclopentanedione
2-(2',4'-dimethylphenyl)-4-nitromethyl-1,3-cyclopentanedione
2-(2'-chloro-4'-methylphenyl)-4-methylthiomethyl-1,3-cyclopentanedione
2-(2'-methylphenyl)-4-(n-propylsulfinylmethyl)-1,3-cyclopentanedione
2-(2'-chloro-4',5'-dimethylphenyl)-4-phenylsulfonylmethyl-1,3-cyclopentanedione
2-(2'-fluoro-4'-methylphenyl)-4-diethylaminomethyl-1,3-cyclopentanedione
2-(2'-methyl-4'-methoxyphenyl)-4-(3'-chlorophenyl)-1,3-cyclopentanedione
8-(2',4'-dimethylphenyl)-bicyclo[4.3.0]nonane-7,9-dione
8-(2'-chloro-5'-methylphenyl)-bicyclo[4.3.0]nonane-7,9-dione
8-(2'-methylphenyl)-2-methyl-bicyclo[4.3.0]nonane-7,9-dione
8-(2',4'-dichlorophenyl)bicyclo[4.3.0]non-3-en-7,9-dione
8-(2'-chloro-4'-methylphenyl)bicyclo[4.3.0]none-3-en-7,9-dione
2-(2',4'-dimethylphenyl)-4,5,6,7-tetrahydro-1,3-indandione
2-(2',5'-dimethylphenyl)-4,5,6,7-tetrahydro-1,3-indandione
4-(2',4'-dimethylphenyl)-tricyclo[5.2.1.0$^{2,6}$]decane-3,5-dione
3-(2'-methylphenyl)-bicyclo[3.3.0]2,4-octanedione
3-(2',4'-dichlorophenyl)-bicyclo[3.2.0]-2,4-heptanedione
2-(2'-methyl-4'-methoxyphenyl)-4-methyl-5-isopropyl-1,3-cyclopentanedione
2-(2'-chloro-4'-trifluoromethylphenyl)-4-(n-propyl)-5-methyl-1,3-cyclopentanedione
2-(2'-methyl-4'-cyanophenyl)-4-methyl-1,3-cyclopentanedione
8-(2'-methyl-4-dimethylaminophenyl)-bicyclo[4.3.0]nonane-7,9-dione
2-(2',4'-dimethylphenyl)-spiro[4.5]decane-1,3-dione
2-(2'-chloro-4'-methoxyphenyl)-spiro[4.4]nonane-1,3-dione
3-(2',5'-dimethylphenyl)-bicyclo[3.3.0]-5-octene-2,4-dione
2-(2'-chloro-4'-methylphenyl)-bicyclo[3.2.0]hept-4-en-1,3-dione pyridinium salt of 2-(2',4'-dimethylphenyl)-1,3-cyclopentanedione
sodium salt of 2-(2',4'-dichlorophenyl)-1,3-cyclopentanedione
triethylammonium salt of 2-(2',4'-dimethylphenyl)-1,3-cyclopentanedione
N-methylpiperidinium salt of 2-(2'-methyl-4'-methoxyphenyl)-4-(4'-chlorophenyl)-1,3-cyclopentanedione
Trimethylammonium salt of 8-(2',5'-dichlorophenyl)-bicyclo[4.3.0]nonane-7,9-dione
morpholinium salt of 2-(2'-methoxyphenyl)-4-methyl-1,3-cyclopentanedione
benzyldimethylammonium salt of 2-(2',4'-dichlorophenyl)-4-(n-propyl)-1,3-cyclopentanedione
dicyclohexylammonium salt of 3-(2'-chloro-4'-methylphenyl)bicyclo[3.3.0]-2,4-octanedione
N,N-diemthylanilinium salt of 2-(2'-chlorophenyl)-4-(n-hexyl)-1,3-cyclopentanedione
2-picolinium salt of 8-(2'-methylphenyl)-bicyclo[4.3.0]nonane-7,9-dione
piperazinium salt of 2-(2',5'-dichloro-4'-methylphenyl)-1,3-cyclopentanedione
imidazolium salt of 2-(2'-methyl-4'-methoxyphenyl)-4-methyl-1,3-cyclopentanedione 8-(2'-methyl-4'-trifluoromethylphenyl)bicyclo[4.3.0]non-3-en-7,9-dione
8-(2',4'-dimethylphenyl)bicyclo[4.3.0]non-5-en-7,9-dione
8-(2'-chlorophenyl)bicyclo[4.3.0]non-5-en-7,9-dione
2-(2',4'-dichlorophenyl)-4-cyclohexyl-1,3-cyclopentanedione
2-(2',5'-dimethylphenyl)-4-methyl-5-isoamyl-1,3-cyclopentanedione
2-(2'-bromophenyl)-4-(2',4'-bromophenyl)-4-(2',4'-dichlorophenyl)-1,3-cyclopentanedione
8-(2'-methyl-4'-n-propylphenyl)bicyclo[4.3.0]non-3-en-7,9-dione
2-(2'-chloro-4',5'-dimethylphenyl)-4-t-butyl-1,3-cyclopentanedione
4-(2',4'-dichlorphenyl) tricyclo[5.2.1.0$^{2.6}$]dec-8-en-3,5-dione
2-(2'-bromo-4'-trifluoromethylphenyl)-4-methoxymethyl-1,3-cyclopentanedione
2-(2'-methylphenyl)-4-(2-ethoxyethyl)-1,3-cyclopentanedione
2-(2',4'-dimethylphenyl)-4-(3-chloropropyl)-1,3-cyclopentanedione
2-(2',5'-dimethylphenyl)-4-(2-nitroethyl)-1,3-cyclopentanedione
2-(2'-bromo-4'-methylphenyl)-4-(3-methyl-2-butenyl)-1,3-cyclopentanedione
2-(2',4'-dibromophenyl)-4-(4'-chlorobenzyl)-1,3-cyclopentanedione
2-(2'-methylphenyl)-4-(2',6'-difluorobenzyl)-1,3-cyclopentanedione
2-(2',5'-dichlorophenyl)-4-(3,3-dichloro-2-propenyl)-1,3-cyclopentanedione
2-(2',4'-dimethylphenyl)-4-cyclopentylmethyl-1,3-cyclopentanedione
2-(2'-methyl-4'-ethylphenyl)-4-(phenylsulfinylmethyl)-1,3-cyclopentanedione
2-(2'-bromophenyl)-4-(ethylsulfonylmethyl)-1,3-cyclopentanedione
2-(2',4'-dimethylphenyl)-4-(2-dimethylaminomethyl)-1,3-cyclopentanedione The following specific examples are presented to more particularly illustrate the novel process of this invention and its use in preparing the novel compounds of this invention.

EXAMPLE I

Preparation of 2-(2',4'-Dichlorophenyl)-1,3-cyclopentanedione 2-(2',4'-Dichlorophenyl)-1,3-cyclopentanedione was prepared from ethyl 5-(2',4'-dichlorophenyl)-4-ketopentanoate utilizing the preparation of Method I. Parts A, B, and C describe the three step preparation of the ethyl 5-(2',4'-dichlorophenyl)-4-ketopentanoate which is used as a starting material in the preparation of 2-(2',4'-Dichlorophenyl)-1,3-cyclopentanedione by Method 1.

Part A: Preparation of ethyl 5-(2',4'-dichlorophenyl)-5-cyano-4-ketopentanoate

A clean, dry 500 ml 3-neck R.B. flask was equipped with a reflux condenser, mechanical stirrer, addition funnel, and nitrogen inlet. The flask was charged with 600 ml of ethanol (distilled from magnesium turnings and stored over type 3A molecular sieves) followed by 30.0 g (1.30 mol) of sodium, and the reaction mixture stirred and heated until all the sodium had dissolved. The temperature of the reaction mixture was then raised to the reflux point, and a mixture of 186.03 g (1.00 mol) of 2,4-dichlorobenzyl cyanide and 261.3 g (1.50 mol) of diethylsuccinate added at a rapid drop rate through the addition funnel. The reaction mixture was refluxed for 12 hours, then approximately ⅔ of the ethanol was distilled off, the reaction mixture refluxed for two additional hours, cooled to room temperature, and poured into 600 ml of ice water. The basic solution was extracted twice with 300 ml of ether, and then acidified with 6 N HCl. An oil formed, and the aqueous acid solution was extracted twice with 250 ml portions of ether. The ether extract was washed twice with water, dried (MgSO$_4$), and the ether stripped to leave 156.61 g (50% yield) of product as a viscous red oil.

Part B: Preparation of 5-(2',4'-dichlorophenyl)-4-ketopentanoic acid

A 1-liter 1-neck R.B. flask was charged with 156.61 g (0.50 Mol) of ethyl-5-(2',4'-dichlorophenyl)-5-cyano-4-ketopentanoate, 153 ml of concentrated sulfuric acid, 153 ml of water, and 440 ml of glacial acetic acid. The reaction mixture was stirred and refluxed for 24 hours. 1 g, 80% yield) was obtained as a viscous dark-colored oil.

Part C: Preparation of ethyl 5-(2',4'-dichlorophenyl)-4-ketopentanoate.

A 1-liter R.B. flask was equipped with a magnetic stirrer and charged with 104.13 g (0.400 mol) of 5-(2',4'-dichlorophenyl)-4-ketopentanoic acid dissolved in 250 ml of ethanol and 250 ml of toluene. To this solution was added 5 ml of concentrated sulfuric acid, and the reaction mixture was refluxed through a Soxhlet extractor containing 300 g of Type 3A molecular sieves for 24 hours. The mixture was cooled and 300 ml of the solvent removed on the Rotary Evaporator. The residue was taken up in 300 ml of ether and washed once with water. The mixture was extracted twice with 150 ml portions of 10% K$_2$CO$_3$ solution, then washed with saturated salt solution, and dried (MgSO$_4$). The solvent was removed on the Rotary Evaporator, and the residue vacuum distilled. The product (52.97 g, 46% yield)

was obtained as a slightly yellow viscous oil, b.p. 124°–165° C./0.10–0.30 mm.

Part D: Preparation of 2-(2′,4′-dichlorophenyl)-1,3-cyclopentanedione

A 1-liter 4-neck R.B. flask was equipped with a mechanical stirrer, Dean-stark trap, reflux condenser with $N_2$ inlet, and thermometer. The flask was charged with 300 ml of ethanol (distilled from magnesium), and 12.53 g (0.545 mol) of sodium was added. The mixture was warmed as necessary to dissolve the sodium. When the sodium had dissolved, the ethanol was distilled off via the Dean-stark trap, and the white, powdery sodium ethoxide was heated to 90° C. to remove the last traces of ethanol. At this time, 250 ml of toluene was added, and distillate was collected and discarded until the vapor temperature was 110° C. If necessary, fresh dry toluene was added to maintain the toluene level at 150–200 ml. The ethyl 5-(2′,4′-dichlorophenyl)-4-ketopentanoate, dissolved in 50 ml of dry toluene, was added, dropwise, and the reaction mixture refluxed overnight. The reaction mixture was a deep red with a heavy suspension of solid.

The reaction mixture was surrounded by an ice bath and 250 ml of ice water added. The mixture was placed in a separatory funnel, and the toluene layer separated from the basic water layer. The aqueous layer was extracted 3 times with ether, and the ether extracts were combined with the toluene layer and washed 2 times with water. The combined water layers (deep red in color) were acidified with concentrated HCl to give a tacky, light brown precipitate, which was digested by warming at 65° C. for one hour, then filtered. This precipitate was air dried and then washed with methylene chloride until a white powder remained. This material was dried for 3 hours at 100° C. in a vacuum oven to give 27.08 g (60% yield) of a white solid, m.p. 228°–232° C.

EXAMPLE II

Preparation of 2-(2′,5′-Dimethylphenyl)-4-methyl-1,3-cyclopentanedione 2-(2′,5′-Dimethylphenyl)-4-methyl-1,3-cyclopentanedione was prepared from ethyl 5-(2′,5′-dimethylphenyl)-4-keto-2-methyl and 3-methyl pentanoate utilizing the preparation of Method 1. Parts A through C describe the three step preparation of ethyl 5-(2′,5′-dimethylphenyl)-4-keto-2-methyl and 3-methyl pentanoate which are used as starting materials in the preparation of 2-(2′,5′-dimethylphenyl)-4-methyl-1,3-cyclopentanedione by Method 1.

Part A: Preparation of ethyl 2-methyl-4-keto-5-cyano-5-(2′,5′-dimethylphenyl) pentanoate and ethyl 3-methyl-4-keto-5-cyano-(2′,5′-dimethylphenyl) pentanoate This material was prepared using 141.16 g (0.750 mol) of diethyl 2-methylsuccinate, 72.60 g (0.500 mol) of 2,5-dimethylbenzyl cyanide, 14.95 g (0.650 mol) of sodium, and 250 ml of dry ethanol using the procedure described in Part A of Example I. The product was obtained as a red oil, 103.20 g (72% yield).

Part B: Preparation of 5-(2′,5′-dimethylphenyl)-4-keto-2-methylpentanoic acid and 5-(2′,5′-dimethylphenyl)-4-keto-3-methylpentanoic acid A mixture of these two acids was prepared by refluxing 103.20 g (0.359 mol) of ethyl 5-(2′,5′-dimethylphenyl)-5-cyano-4-keto-2 and 3-methylpentanoates in 315 ml of glacial acetic acid, 105 ml of concentrated sulfuric acid, and 105 ml of water. The procedure is described in Example I, Part B. The product was obtained as a red oil (51.38 g, 61% yield).

Part C: Preparation of ethyl 5-(2′,5′-dimethylphenyl)-4-keto-2-methyl and 3-methyl pentanoate Using the procedure in Example I, Part C, 51.38 g (0.22 mol) of 5-(2′,5′-dimethylphenyl)-4-keto-2 and 3-methylpentanoic acid was converted to 48.88 g (85% yield) of the ethyl ester. The product was purified by vacuum distillation, b.p. 120° C./0.05 mm, and was obtained as a light yellow, viscous oil.

Part D: Preparation of 2-(2′,5′-dimethylphenyl)-4-methyl-1,3-cyclopentanedione Utilizing 48.88 g (0.186 mol) of ethyl 5-(2′,5′-dimethylphenyl)-4-keto-2 and 3-methylpentanoate, 12.86 g (0.559 mol) of sodium, 250 ml of ethanol, 250 ml of toluene, and the procedure described in Example I, Part D, 27.85 g (69% yield) of 2-(2′,5′-dimethylphenyl)-4-methyl-1,3-cyclopentanedione was obtained as a white, crystalline solid, m.p. 138°–139.5° C., after recrystallization from isopropyl ether - methylene chloride.

EXAMPLE III

Preparation of 2-(2′-Methylphenyl)-4,5,6,7,8,9-hexahydro-1,3-indandione 2-(2′-methylphenyl)-4,5,6,7,8,9,-hexahydro-1,3-indandione was synthesized from 4,5,6,7,8,9-hexahydro-3-(2′-methylphenyl) methylene lactone utilizing the preparation of Method 2. Parts A and B described the two step preparation of the 4,5,6,7,8,9-hexahydro-3-(2′-methylphenyl) methylene lactone which is used as a starting material in the preparation of 2-(2′-methylphenyl)-4,5,6,7,8,9-hexahydro-1,3-indandione by Method 2.

Part A: Preparation of ethyl 2-(α-cyano-2′-methylphenylacetyl)cyclohexyl carboxylate Using the procedure described in Example I, Part A, and starting with 159.80 g (0.700 mol) of diethyl 1,2-cyclohexanedicarboxylate, 61.65 g (0.47 mol) of 2-methylbenzyl cyanide, 14.06 g (0.61 mol) of sodium, and 250 ml of ethanol, 87.74 g (60% yield) of the desired cyano keto ester was obtained as a red, viscous oil.

Part B: Preparation of 4,5,6,7,8,9,-hexahydro-3-(2′-methylphenyl) methylene lactone A 1-liter R.B. flask was equipped with a mechanical stirrer, reflux condenser with nitrogen inlet, and addition funnel. The flask was charged with a solution of 87.74 g (0.28 mol) of ethyl 2-(α-cyano-2′-methylphenylacetyl) cyclohexylcarboxylate in 210 ml of glacial acetic acid, followed by 70 ml of water. This solution was stirred under N₂ and 70 ml of concentrated sulfuric acid was added, dropwise. The reaction mixture was refluxed for 48 hours, cooled to room temperature, and as much of the acetic acid as possible removed on the rotary evaporator. The mixture was diluted with 500 ml of water, and extracted three times with 150 ml of ether. The combined ether layers were washed twice with water, then extracted 6 times with 150 ml portions of 0.5 N NaOH, washed twice with water, dried (MgSO₄), and stripped to leave a slightly yellow solid. This material was recrystallized from isopropyl ether to give 34.61 g (49% yield) of a slightly tan solid.

Part C: Preparation of
2-(2'-methylphenyl)-4,5,6,7,8,9-hexahydro-1,3-indandione

A 500 ml R.B. flask was equipped with a mechanical stirrer, Dean-Stark trap, reflux condenser with N₂ inlet, and addition funnel. All of the glassware was dried thoroughly. The flask was charged with 150 ml of dry ethanol and 6.57 g (0.286 mol) of sodium added. The reaction mixture was heated sufficiently to dissolve the sodium. When the sodium had all dissolved, the ethanol was removed by distillation into the Dean-Stark trap. Toluene (150 ml) was added to the residual, powdery sodium ethoxide, and solvent was distilled off until the vapor temperature was 110° C. Toluene was added slowly during this distillation to maintain the solvent level at 150 ml. The enol lactone prepared in Step B, 34.61 g (0.143 mol) in 75 ml of toluene was added, dropwise, to the reaction mixture at 65° C. After the addition was complete, solvent was distilled off until the vapor temperature reached 110° C. Again toluene was added as necessary to maintain the solvent level at 150 ml. The reaction mixture was cooled to room temperature, surrounded by an ice bath, and 150 ml of ice water added. The aqueous layer was separated from the toluene, and the toluene washed twice with water. The combined basic water layers were extracted twice with ether, then acidified. A tacky tan solid formed which was taken up in 500 ml of methylene chloride, washed 3 times with water, dried (MgSO₄), and stripped to leave a tan solid. This solid was triturated with boiling isopropyl ether and the resulting white, powdery precipitate filtered off and dried at 75° C. in a vacuum oven. The product, 22.38 g (65% yield), was a white solid, m.p. 139°–142° C.

EXAMPLE IV

Preparation of
8-(2',4'-dichlorophenyl)bicyclo[4.3.0]non-3-en-7,9-dione 8-(2',4'-dichlorophenyl)bicyclo[4.3.0]non-3-en-9-dione was prepared from 7-keto-8-(α-hydroxy-2'4'-dichlorobenzyl)-8-trimethylsiloxybicyclo[4.2.0]-3-octene utilizing the preparation of Method 3. Part A describes the preparation of 7-keto-8-(α-hydroxy-2',4'-dichlorobenzyl)-8-trimethylsiloxybicyclo [4.2.0]-3-octene.

Part A: Preparation of 7-keto-8-(α hydroxy-2,4'-dichlorobenzyl)-8-trimethylsiloxybicyclo[4.2.0]-3-octane A mixture of 3.79 g (0.02 mol) of titanium tetrachloride and 3.85 g (0.022 mol) of 2,4-dichlorobenzaldehyde in 350 ml of methylene chloride was cooled to −78° C. Under a nitrogen atmosphere 5.65 g (0.020 mol) of 7,8-bistrimethylsiloxybicyclo[4.2.0]-3,7-octadiene in 15 ml of methylene chloride was added during 40 min. The mixture was stirred at −78° for an additional 30 minutes and then was allowed to warm to room temperature gradually over 2 hours. The mixture was poured into 600 ml of cold water. The layers were separated. The aqueous layer was extracted with 300 ml of ethyl ether. The combined organic layers were dried over MgSO₄, filtered and concentrated under reduced pressure to give 6.34 g (82.26%) of desired product.

Part B: Preparation of 8-(2',4'-dichlorophenyl)bicyclo [4.3.0]non-3-en-7,9-dione A 1-liter R.B. flask was equipped with a magnetic stirrer and charged with 6.34 grams (0.016 mol) of 7-keto-8-(α-hydroxy-2',4'-dichlorobenzyl)-8-trimethylsiloxybicyclo [4.2.0]-3,7-octadiene and 75 ml trifluoroacetic acid. The mixture was stirred at room temperature for 3 days. The mixture was poured in 400 g of ice and extracted four times with 100 ml of methylene chloride. The methylene chloride extracts were combined and concentrated by distillation and extracted four times with 100 ml of ice cold 10% NaOH. The yellow NaOH solution was acidified to a pH of 2–3 with concentrated H₂SO₄ keeping the temperature near 10°–15° C. The acidic aqueous solution was extracted twice with 100 ml of ether, dried over MgSO₄, filtered and concentrated under reduced pressure. The light yellow solid residue was dried under high vacuum for 2–3 hours. The solid was triturated with 40 ml of hot isopropyl ether. The suspension was cooled gradually to room temperature giving 1.16 g (18.3%) of tan solid, m.p. 154–157.

EXAMPLE V

Preparation of
2-(2',4'-dimethylphenyl)-1,3-cyclopentanedione 2-(2',4'-dimethylphenyl)-1,3-cyclopentanedione was prepared from ethyl 5-(2',4'-dimethylphenyl)-4-ketopentanoate utilizing the preparation of Method 1. Parts A, B, and C describe the three step preparation of ethyl 5-(2',4'-dimethylphenyl)-4-ketopentanoate which is used as the starting material in the preparation of 2-(2',4'-dimethylphenyl)-1,3-cyclopentanedione by Method 1.

Part A: Preparation of ethyl
5-(2',4'-dimethylphenyl)-5-cyano-4-ketopentanoate

This material was prepared using 130.65 g (0.750 mol) of diethyl succinate, 72.60 g (0.500 mol) of 2,4-dimethylbenzyl cyanide, 14.95 g (0.65 mol) of sodium, and 168 ml of dry ethanol using the procedure described in Part A of Example I. The product was obtained as a dark red oil, 106.5 g (78% yield).

Part B: Preparation of
5-(2',4'-dimethylphenyl)-4-ketopentanoic acid

This acid was prepared by refluxing 106.5 g (0.390 mol) of ethyl 5-(2',4'-dimethylphenyl)-5-cyano-4-ketopentanoate in 350 ml of glacial acetic acid, 122 ml of water, and 122 ml of concentrated sulfuric acid. The procedure is described in Example I, Part B. The product was obtained as a dark-colored viscous oil, 39.2 g (46% yield).

Part C: Preparation of ethyl 5-(2',4'-dimethylphenyl)-4-ketopentanoate

Using the procedure of Example I, Part C, 39.2 g (0.18 mol) of 5-(2',4'-dimethylphenyl)-4-ketopentanoic acid was converted to 21.46 g. (48% yield) of the ethyl ester. The product was purified by vacuum distillation, b.p. 127°-170° C./0.10-0.50 mm.

Part D: Preparation of 2-(2',4'-dimethylphenyl)-1,3-cyclopentanedione

Utilizing 21.46 g. (0.0864 mol) of ethyl 5-(2',4'-dimethylphenyl)-4-ketopentanoate, 4.00 g. (0.173 mol) of sodium, 125 ml of dry ethanol, 200 ml of toluene, and the procedure described in Example I, Part D, 8.60 g (49% yield) of 2-(2',4'-dimethylphenyl)-1,3-cyclopentanedione was obtained as a white, crystalline solid, m.p. 198.0°-200.5° C.

EXAMPLE VI

Preparation of 2-(2',4'-dimethylphenyl)-4,5,6,7,8,9-hexahydro-1,3-indandione 2-(2',4'-dimethylphenyl)-4,5,6,7,8,9-hexahydro-1,3-indandione was prepared from 4,5,6,7,8,9-hexahydro-3-(2',4'-dimethylphenyl)methylene lactone utilizing the preparation of method 2. Parts A and B describe the two step preparation of the 4,5,6,7,8,9-hexahydro-3-(2',4'-dimethylphenyl)methylene lactone.

Part A: Preparation of ethyl 2-(α-cyano-2',4'-dimethylphenylacetyl)cyclohexyl carboxylate Using the procedure described in Example I, Part A, and starting with 114.14 g (0.500 mol) of diethyl 1,2-cyclohexanedicarboxylate, 43.72 g. (0.333 mol) of 2,4-dimethylbenzyl cyanide, 10.0 g (0.433 mol) of sodium, and 115 ml of dry ethanol, 58.27 g (53% yield) of the desired cyano keto ester was obtained as a red viscous oil.

Part B: Preparation of 4,5,6,7,8,9-hexahydro-3-(2',4'-dimethylphenyl)methylene lactone Using the procedure described in Example III, Part B, and starting with 109.42 g (0.334 mol) of ethyl 2-(α-cyano-2',4'-dimethylphenylacetyl)cyclohexyl carboxylate, 350 ml of glacial acetic acid, 109 ml of concentrated sulfuric acid, and 109 ml of water, a total of 25.33 g (30% yield) of the methylene lactone, m.p. 102°-103° C., was obtained after recrystallization from isopropyl ether.

Part C: Preparation of 2-(2',4'-dimethylphenyl)-4,5,6,7,8,9-hexahydro-1,3-indandione Using the procedure described in Example III, Part C, and starting with 22.67 g (0.0884 mol) of 4,5,6,7,8,9-hexahydro-3-(2',4'-dimethylphenyl) methylene lactone, 4.07 g (0.177 mol) of sodium, 100 ml of dry ethanol, and 200 ml of toluene, a total of 11.45 g (51% yield) of dione was obtained as a white solid after recrystallization from isopropyl ether with a melting point of 168°-169° C.

EXAMPLE VII

Preparation of 2-(2',5'-dimethylphenyl)-4,5,6,7,8,9-hexahydro-1,3-indandione 2-(2',5'-dimethylphenyl)-4,5,6,7,8,9-hexahydro-1,3-indandione was prepared from 4,5,6,7,8,9-hexahydro-3-(2',5'-dimethylphenyl)methylene lactone utilizing the preparation of method 2. Parts A and B describe the two step preparation of the 4,5,6,7,8,9-hexahydro-3-(2',5'-dimethylphenyl)methylene lactone.

Part A: Preparation of ethyl 2-(α-cyano-2',5'-dimethylphenylacetyl)cylohexyl carboxylate Using the procedure described in Example I, Part A, and starting with 159.80 g (0.700 mol) of diethyl 1,2-cyclohexanedicarboxylate, 61.21 g (0.47 mol) of 2,5-dimethylbenzyl cyanide, 14.06 g (0.61 mol) of sodium, and 250 ml of dry ethanol, 50.42 g (33% yield) of the cyano keto ester was obtained as a yellow, viscous oil.

Part B: Preparation of 4,5,6,7,8,9-hexahydro-3-(2',5'-dimethylphenyl)methylene lactone Using the procedure described in Example III, Part B, and starting with 116.17 g (0.355 mol) of ethyl 2-(2-cyano-2',5'-dimethylphenylacetyl)cyclohexylcarboxylate, 110 ml of conc. sulfuric acid, 110 ml of water, a total of 50.38 g (55% yield) of the desired methylene ketone, m.p. 88°-90° C. was obtained.

Part C: Preparation of 2-(2',5'-dimethyphenyl)-4,5,6,7,8,9-hexahydro-1,3-indandione Using the procedure described in Example III, Part C, and starting with 50.00 g (0.195 mol) of 4,5,6,7,8,9-hexahydro-3-(2',5'-dimethylphenyl) methylene lactone, 13.46 g (0.585 mol) of sodium, 250 ml of dry ethanol, and 250 ml of toluene, a total of 21.88 g (44% yield) of the desired dione was obtained as a powdery white solid, m.p. 145°-147° C.

Additional compounds synthesized utilizing the above methods are included in Table I, below.

Selected 2-aryl-1,3-cyclopentanedione compounds, representative of those useful in accordance with this invention were tested with respect to their miticidal, mite ovicidal and pre-emergent and post-emergent herbicidal activity. It was found that the compounds of the instant invention exhibited improved pesticidal activity, in particular, miticidal activity, over structurally similar prior art compounds.

Suspensions of the test compounds were prepared by dissolving one gram of compound in 50 milliliters of acetone in which had been dissolved 0.1 gram (10 percent of the weight of compound) of an alkylphenoxyethanol surfactant, as an emulsifying or dispersing agent. The resulting solution was mixed into 160 milliliters of water to give roughly 200 milliliters of a suspension containing the compound in finely divided form. The thus prepared stock suspension contained 0.5 percent by weight of compound. The test concentrations employed in the tests described herein below were obtained by diluting the stock suspension with water. The test procedures were as follows:

Mite Foliage Spray Test

Adults and nymphal stages of the two-spotted mite (*Tetranychus urticae* (Koch)), reared on Tendergreen bean plants at 80°±5° F. and 50±5 percent relative humidity, were the test organisms. Infested leaves from a stock culture were placed on the primary leaves of two bean plants six to eight inches in height, growing in a two-and-a-half inch clay pot. 150-200 Mites, a sufficient number for testing, transferred from the excised leaves to the fresh plants in a period of twenty-four hours. Following the twenty-four hour transfer period, the excised leaves were removed from the infested plants. The test compounds were formulated by diluting the stock suspension with water to provide suspensions containing the desired amount of test compound per million parts of final formulation. The potted plants (one pot per compound) were placed on a revolving turntable and sprayed with 100-110 milliliters of test compound formulation by use of a DeVilbis spray gun set at 40 psi. air pressure. This application, which lasted 30 seconds, was sufficient to wet the plants to run-off. As a control, 100-110 milliliters of a water solution containing acetone and emulsifier in the same concentrations as the test compound formulation, but containing no test compound, were also sprayed on infested plants. The sprayed plants were held at 80°±5° F. and 50±5 percent relative humidity for four days, after which, a mortality count of motile forms was made on the leaves of the test plants. Any individual which was capable of locomotion upon prodding was considered living.

Mite Ovicide Test

The test organism was the egg of the two-spotted mite (*Tetranychus urticae* (Koch)), as obtained from adults reared on Tendergreen bean plants under controlled conditions of 80°±5° F. and 50±5 percent relative humidity. Heavily infested leaves from a stock culture were placed on the primary leaves of two bean plants six to eight inches in height growing in a two-and-a-half inch clay pot. Females were allowed to oviposit for a period of 48 hours and then the leaves of the infested plants were dipped in a solution containing 800 parts of tetraethyl pyrophosphate per million parts of water in order to destroy the reproductory forms and thus prevent further egg laying. This solution of tetraethyl pyrophosphate does not affect the viability of the eggs. The plants were allowed to dry thoroughly. The test compounds were formulated by diluting the stock suspension with water to give a suspension containing varying amounts of test compound per million parts of final formulation. The plotted plants (one pot per compound) were placed on a revolving turntable and sprayed with 100-110 milliliters of test compound formulation by use of a DeVilbis spray guns set at 40 spig. air pressure. This application which lasted 30 seconds, was sufficient to wet the plants to run-off. As a control, 100-110 milliliters of a water solution containing acetone and emulsifier in the same concentrations as the test compound formulation, but containing no test compound, were also sprayed on plants infested with eggs. The sprayed plants were held at 80°±5° F. and 50±5 percent relative humidity for four days, after which a microscopic examination was made of unhatched (dead) and hatched (living) eggs.

In these tests the pesticidal activity of the compounds against mites and mite eggs was rated as follows:

A = Excellent Control
B = Partial Control
C = No Control

PRELIMINARY HERBICIDE SEED GERMINATION TEST

The following seeds were used in this test:
Perennial rye grass—*Solium perenne*
Crabgrass—*Digitaria sanguinalis*
Red root pigweed—*Amaranthus retroflexus*
Mustard—*Brassica pincea var. foliosa* (Florida broadleaf)

Two seed-oil mixtures were prepared as follows:

| Mixture I | 196 cc. | Rye grass seed |
|---|---|---|
| | 75 cc. | Mustard seed |
| | 18,000 cc. | Sifted, fairly dry soil |
| Mixture II | 99 cc. | Crabgrass seed |
| | 33 cc. | Amaranthus |
| | 18,000 cc. | Sifted, fairly dry soil |

Each of the above mixtures was rolled separately in 5 gallon containers for approximately one-half hour on ball mill to insure uniform mixing of seeds and soil. For each compound four 3-inch pots were filled with soil to within 1½ inches of top of pots. To two of these pots were added 70 cc. of Mixture I. To the remaining 2 pots were added 70 cc. of Mixture II. The seed-soil mixture was tamped firmly, and the pots were removed to the green-house and watered lightly. About 2 hours after planting, 25 milliliters of the test formulation were added to one pot containing Mixture I and one pot containing Mixture II. An equal volume of a water solution containing acetone and an emulsifier in the same concentration as the herbicidal mixture but without the candidate herbicide was also added to each of the soil-seed mixtures. These pots are used as check or control units. The test compounds were formulated by diluting the stock suspension with water to obtain the desired concentration of the compound in parts per million of the final formulation. Each compound was tested at the same concentration. Ten to twelve days after application of the chemical, injury was noted for each species by comparing treated vs. untreated pots. Ratings were made according to the following designations:

5 = no seedling emerged
4 = few seedlings emerged and/or very severe stunting
3 = moderate reduction in stand and/or moderate stunting
2 = very slight reduction in stand and/or slight stunting
1 = no injury; seedlings appear no different with respect to stand or growth than untreated controls.

POST-EMERGENT HERBICIDAL TEST

Experiments were also conducted to determine the phytotoxicity of representative compositions with respect to healthy fresh plants. Solutions of the compounds were prepared as described above to provide a concentration of 2500 parts per million of the test compound. The test plants were sprayed in accordance with the procedure described above for the Mite Foliage Spray Test so as to deliver approximately 100 milliliters of test solutions to the leaves of each plant tested. The sprayed plants and controls were set aside for approximately one hour to allow the solutions to dry and were then placed in the greenhouse. After ten days the plants were visually inspected to determine the extent of foliage injury. A rating of 1 indicates no perceptible injury; 5 indicates the plant was dead and ratings of 2, 3 and 4 indicate intermediate degrees of injury based upon the number and extent to which leaves were injured.

The results of these experiments are summarized and set forth in Table I below.

powders the aforementioned dispersing agents as well as lignosulfonates can be included.

The required amount of the toxicants contemplated herein may be applied per acre treated in from 1 to 200 gallons or more of liquid carrier and/or diluent or in from about 5 to 500 pounds of inert solid carrier and/or diluent. The concentration in the liquid concentrate will usually vary from about 10 to 95 percent by weight and in the solid formulations from about 0.5 to about 90

TABLE I

BIOLOGICAL ACTIVITY OF 2-ARYL-1,3-CYCLOPENTANEDIONE COMPOUNDS

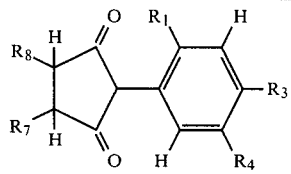

| | | | | | | Miticidal | | Post-Emergent Herbicidal | | | | | Pre-emergent Herbicidal | | |
|---|---|---|---|---|---|---|---|---|---|---|---|---|---|---|---|
| $R_1$ | $R_3$ | $R_4$ | $R_7$ | $R_8$ | MP(°C.) | Adult | Egg | Bean | Corn | Tomato | Cotton | Soybean | Rye | Crabgrass | Amaranthus | Mustard |
| Cl | H | H | H | H | 197–199 | B | C | 3 | 2 | 1 | 2 | 1 | 5 | 3 | 1 | 3 |
| Cl | Cl | H | H | H | 288–232 | A | B | 1 | 1 | 1 | 2 | 1 | 1 | 1 | 1 | 1 |
| $CH_3$ | H | H | H | H | 173–176 | A | B | 3 | 3 | 2 | 3 | 1 | 5 | 2 | 1 | 1 |
| $CH_3$ | $CH_3$ | H | H | H | 198–200.5 | A | A | 1 | 2 | 1 | 1 | 1 | 5 | 5 | 5 | 3 |
| $CH_3$ | H | $CH_3$ | H | H | 142–143.5 | A | B | 2 | 2 | 1 | 2 | 3 | 4 | 2 | 3 | 2 |
| $CH_3$ | H | $CH_3$ | $CH_3$ | H | 138–139.5 | A | B | 2 | 3 | 2 | 2 | 2 | 4 | 2 | 3 | 2 |
| $CH_3$ | H | H | $-(CH_2)_4-$ | | 139–142 | A | A | 2 | 2 | 1 | 3 | 1 | 5 | 3 | 3 | 2 |
| $CH_3$ | $CH_3$ | H | $-(CH_2)_4-$ | | 168–169 | A | A | 1 | 2 | 2 | 2 | 5 | 5 | 5 | 5 | 5 |
| $CH_3$ | H | $CH_3$ | $-(CH_2)_4-$ | | 145–147 | A | A | 1 | 1 | 1 | 1 | 1 | 1 | 1 | 1 | 1 |
| Cl | Cl | H | $-(CH_2CHCHCH_2)$ | | 154–157 | A | A | — | — | — | — | — | — | — | — | — |

It will be understood that the plant species employed in the above tests are merely representative of a wide variety of plant pest that can be controlled by the use of the compounds of this invention. The compounds contemplated in this invention may be applied as acaricides and pre-emergent and post-emergent herbicides according to methods known to those skilled in the art. Pesticidal compositions containing the compounds as the active toxicant will usually comprise a carrier and/or diluent, either liquid or solid.

Suitable liquid diluents or carriers include water, petroleum distillates, or other liquid carriers with or without surface active agents. Liquid concentrates may be prepared by dissolving one of these compounds with a nonphytotoxic solvent such as acetone, xylene, or nitrobenzene and dispersing the toxicants in water with the aid of suitable surface active emulsifying and dispersing agents.

The choice of dispersing and emulsifying agents and the amount employed is dictated by the nature of the composition and the ability of the agent to facilitate the dispersion of the toxicant. Generally, it is desirable to use as little of the agent as is possible, consistent with the desired dispersion of the toxicant in the spray so that rain does not re-emulsify the toxicant after it is applied to the plant and wash it off the plant. Nonionic, anionic, amphoteric or cationic dispersing and emulsifying agents may be employed, for example, the condensation products of alkylene oxides with phenol and organic acids, alkyl aryl sulfonates complex ether alcohols, quaternary ammonium compounds, and the like.

In the preparation of wettable powder or dust or granulated compositions, the active ingredient is dispersed in and on an appropriately divided solid carrier such as clay, talc, bentonite, diatomaceous earth, fullers earth, and the like. In the formulation of the wettable percent by weight. Satisfactory sprays, dusts, or granules for general use contain from about ¼ to 15 pounds of active toxicant per acre.

The pesticides contemplated herein prevent attack by acarids, particularly mites, upon plants or other material to which the pesticides are applied, and they have relatively high residual toxicity. With respect to plants, they are relatively safe to plants when used in sufficient amount to kill or repel the acarids or other pests, and they resist weathering which includes wash-off caused by rain, decomposition by ultraviolet light oxidation, or hydrolysis in the presence of moisture or, at least such decomposition, oxidation, and hydrolysis as would materially decrease the desirable pesticidal characteristic of the toxicants. The toxicants are so chemically inert that they are compatible with substantially any other constituents of the spray schedule. Mixtures of the active compounds may be employed if desired as well as combinations of the active compounds of this invention with other biologically active compounds.

What is claimed is:

1. A method of preparing a compound of the formula:

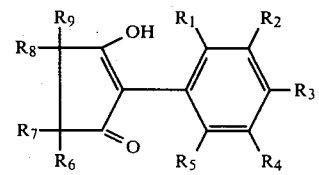

which comprises reacting in a toluene solvent a compound of the formula:

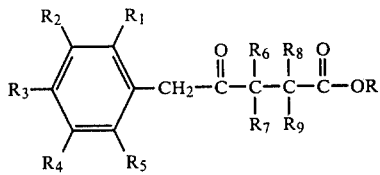

with a sodium ethoxide base; wherein:

R is a $C_1$–$C_4$ alkyl group;

$R_1$ is an alkyl, haloalkyl, halogen or polyhaloalkyl group:

$R_2$, $R_3$, $R_4$, and $R_5$ are individually hydrogen, or a nitro, polyhaloalkyl, halogen, cyano, alkyl, alkoxy, alkylthio, alkylsulfinyl, alkylsulfonyl, alkanoyl, amido, amino or haloalkyl group;

$R_6$, $R_7$, $R_8$, and $R_9$ are individually hydrogen, or either an unsubstituted or substituted alkyl, alkenyl, cycloalkyl, cycloalkenyl or phenyl group wherein the permissible substituents are one or more alkyl, alkanoyl, cycloalkyl, cycloalkenyl, cyano, halogen, nitro, alkoxy, aryloxy, alkylthio, arylthio, alkylsulfinyl, alkylsulfonyl, acylamido or dialkylamino groups;

with the provisos that $R_1$, $R_2$, $R_3$, $R_4$, $R_5$, $R_6$, $R_7$, $R_8$ and $R_9$ substituents individually may not include more than ten aliphatic carbon atoms.

2. The method of claim 1 wherein:

the reaction is conducted at a temperature from 100° C. to 125° C.

* * * * *

UNITED STATES PATENT AND TRADEMARK OFFICE
CERTIFICATE OF CORRECTION

PATENT NO. : 4,283,348

DATED : August 11, 1981

INVENTOR(S) : Thomas N. Wheeler

It is certified that error appears in the above—identified patent and that said Letters Patent is hereby corrected as shown below:

Column 1, line 37 "alkylsulfnyl" should read --alkylsulfonyl--

Column 9, line 25, 8-(2'methyl-4'-trifluoromethylphenol)bicyclo [4.3.0] non-3-en-7,9-dione should be listed as separate compound Column 9, line 35 "2-(2'bromophenyl)-4-(2',4'-bromophenyl)-4-(2',4-dichlorophenyl)-1,3-cyclopentanedione" should read --2-(2'-bromophenyl)-4-(2',4'-dichlorophenyl)-1,3-cyclopentanedione--

Column 10, line 49, Before "80% yield" should read -- The reaction mixture was cooled to room temperature and 300 ml of water was added followed by 200 ml of isopropyl ether. The mixture was refluxed for 1/2 hour, cooled in an ice bath, and filtered. The desired acid (104.13g, --.

UNITED STATES PATENT AND TRADEMARK OFFICE
CERTIFICATE OF CORRECTION

PATENT NO. : 4,283,348　　　　　　　　　　　　Page 2 of 2
DATED : August 11, 1981
INVENTOR(S) : Thomas N. Wheeler It is certified that error appears in the above—identified patent and that said Letters Patent is hereby corrected as shown below:

mixture was reflexed for 1/2 hour, cooled in an ice bath, and filtered. The desired acid (104,13g,--.

"1 g," on column 10, line 49 should be deleted.

Column 11, line 39 "27.08 g" should read --26.08g--

Signed and Sealed this

Twelfth Day of January 1982

[SEAL]

Attest:

GERALD J. MOSSINGHOFF

*Attesting Officer*　　　*Commissioner of Patents and Trademarks*